(12) United States Patent
Biancalani et al.

(10) Patent No.: US 8,043,559 B2
(45) Date of Patent: Oct. 25, 2011

(54) SYSTEM FOR TEMPERATURE CONTROL WITHIN AN AUTOMATIC BIOLOGICAL ANALYZER

(75) Inventors: Maurizio Biancalani, Calenzano (IT); Giovanni Alunni, Florence (IT); Gabriele Ricci, Monte san Savino (IT)

(73) Assignee: Bio Merieux, Marcy l'Etoile (FR)

( * ) Notice: Subject to any disclaimer, the term of this patent is extended or adjusted under 35 U.S.C. 154(b) by 974 days.

(21) Appl. No.: 10/557,175

(22) PCT Filed: May 19, 2004

(86) PCT No.: PCT/FR2004/050202
§ 371 (c)(1), (2), (4) Date: Aug. 11, 2006

(87) PCT Pub. No.: WO2004/109294
PCT Pub. Date: Dec. 16, 2004

(65) Prior Publication Data
US 2006/0275175 A1 Dec. 7, 2006

(30) Foreign Application Priority Data
May 28, 2003 (FR) ..................................... 03 06477

(51) Int. Cl.
*C12Q 1/68* (2006.01)
*G01N 21/00* (2006.01)
(52) U.S. Cl. .......................................... 422/50; 422/64
(58) Field of Classification Search .................... 422/50, 422/64
See application file for complete search history.

(56) References Cited

U.S. PATENT DOCUMENTS

| | | | |
|---|---|---|---|
| 3,616,264 A * | 10/1971 | Ray et al. .................. | 435/287.3 |
| 4,647,432 A | 3/1987 | Wakatake | |
| 4,774,055 A | 9/1988 | Wakatake et al. | |
| 5,133,936 A | 7/1992 | Umetsu et al. | |
| 5,145,646 A * | 9/1992 | Tyranski ....................... | 422/547 |
| 5,171,531 A | 12/1992 | Christianson et al. | |
| 5,849,247 A | 12/1998 | Uzan et al. | |
| 6,156,565 A * | 12/2000 | Maes et al. ................. | 435/287.3 |
| 2003/0053933 A1 | 3/2003 | Miyake et al. | |

FOREIGN PATENT DOCUMENTS

| | | |
|---|---|---|
| EP | 0 837 331 A1 | 4/1998 |
| EP | 0 864 866 A1 | 9/1998 |

(Continued)

*Primary Examiner* — Lore Jarrett
(74) *Attorney, Agent, or Firm* — Oliff & Berridge, PLC

(57) ABSTRACT

The present invention relates to a system for temperature control within an automatic biological analyzer, the automatic analyzer essentially comprising:
support, guidance, and step-by-step transport means for reaction cuvettes on a path comprising a predetermined number of positions,
a support turntable for analyte samples,
a support turntable for reactants, means for taking defined quantities of samples and reactants and for injecting the same into the reaction cuvettes,
means for washing the cuvettes,
means for optical reading of the determination results and a computerized control system which permits carrying out pre-programmed analysis cycles.
It consists in the fact that the temperature control system is connected to the lower part of the support turntable for the analyte samples, said system comprising within itself:
at least one inlet air deflector,
at least one outlet air deflector,
a circular air transfer path positioned between the inlet deflector and the outlet deflector, and
means for generating circulating air in the circular path, thereby permitting a reduction in the thermal variation between the inlet air and outlet air temperatures within the temperature control system.
The invention finds a preferential application in the diagnostic field.

12 Claims, 2 Drawing Sheets

FOREIGN PATENT DOCUMENTS

| | | |
|---|---|---|
| EP | 1 102 068 A1 | 5/2001 |
| WO | WO 91/07662 A1 | 5/1991 |
| WO | WO 96/14582 A1 | 5/1996 |
| WO | WO 00/16075 A1 | 3/2000 |

\* cited by examiner

SYSTEM FOR TEMPERATURE CONTROL WITHIN AN AUTOMATIC BIOLOGICAL ANALYZER

The invention relates to an apparatus for immunological determination of various substances in biological samples, permitting automation of the determination methods of the ELISA, RIA, FIA, LIA, FPIA, CLIA type, etc. More precisely, the invention relates to a system for temperature control of determination reactants within said determination apparatus.

Apparatus of this type are already described in applications WO-A-91/07662 and WO-A-96/14582, belonging to the applicant, containing a description of the determinations carried out, these known apparatus essentially comprising support, guidance and step-by-step transport means for reaction cuvettes on a path comprising a predetermined number of positions, a support turntable for analyte samples, a support turntable for reactants, means for taking defined quantities of samples and reactants and for injecting the same into the reaction cuvettes, means for washing the cuvettes, means for optical reading of the determination results and a computerized control system which permits the carrying out of pre-programmed analysis cycles, corresponding to determinations of the monoreactant or bireactant type, these known apparatus having an operating rate of about 120 determinations per hour for the former and 360 determinations per hour for the latter.

However, in these immunological determination apparatus, nothing is provided for maintaining the support turntable for the determination reactants at a sufficiently low temperature to be compatible with the preservation thereof, in order to guarantee the maintenance of the optimal reaction conditions.

Patent application EP-A-0 864 866 relates to an automatic machine similar to the one for which the temperature control system of the present invention is suitable. The air transfer path therein is very important. To maintain the temperature at a suitable value, it is recommended to use an air cooling unit that procures cooled air forced into a housing, such as a cover (see in this regard FIGS. 29 and 30 of the description, page 9, lines 8 to 10).

Such a solution is unsuitable for a rather long air transfer path, because the temperature difference between the cold air inlet and the hot air outlet is rather wide. This temperature gradient is obviously detrimental to the biological results that could be obtained by the automatic analyzer.

In light of this prior art, it is a major object of the present invention to propose a system permitting the control and maintenance of the temperature of the reactants used in an automatic analyzer, at a constant value, regardless of the position of the reactants, and throughout the analysis.

A further major object of the present invention is to propose a system permitting control of the temperature of the reactants present in open containers, based on the circulation of refrigerated air that does not cause evaporation of the reactants.

According to the present invention, a temperature control system is proposed within an automatic biological analyzer, which serves to achieve the above objects.

For this purpose, the present invention hence relates to a system for temperature control within an automatic biological analyzer, the automatic analyzer essentially comprising:
support, guidance, and step-by-step transport means for reaction cuvettes on a path comprising a predetermined number of positions,
a support turntable for analyte samples,
a support turntable for reactants, means for taking defined quantities of samples and reactants and for injecting the same into the reaction cuvettes,
means for washing the cuvettes,
means for optical reading of the determination results and a computerized control system which permits carrying out pre-programmed analysis cycles,
said temperature control system being characterized in that it is connected to the lower part of the support turntable for the determination reactants, said system comprising within itself:
at least one inlet air deflector,
at least one outlet air deflector,
a circular air transfer path positioned between the inlet deflector and the outlet deflector, and
means for generating circulating air in the circular path,
thereby permitting a reduction in the thermal variation between the inlet air and outlet air temperatures within the temperature control system.

In a preferred embodiment, the system is formed by a cover of substantially annular shape with a U cross section.

In a preferred embodiment, the system is formed by a cover which has an outer vertical wall, an inner vertical wall and a lower horizontal wall, the upper side of the horizontal wall being substantially plane.

According to the latter embodiment, the horizontal wall is perforated with at least two openings located substantially at 180° to one another along the circular air transfer path and the air deflectors are arranged on the upper side of said horizontal wall over said openings.

In all the above cases, it is advantageous for each air deflector to consist of an upper plate and at least one spacer connecting the horizontal wall to said plate.

Moreover, the upper plate may be substantially parallel to the upper side of the horizontal wall.

Also in all the above cases, the lower part of the support turntable for determination reactants is perforated and extends into the temperature control system.

Preferably, the determination reactants present in containers, such as bottles or jars, are only present in the openings in the perforated turntable.

The figures appended hereto are given as explanatory examples and are nonlimiting. They permit a clearer understanding of the invention.

The temperature control system is positioned within an automatic biological analyzer. This automatic analyzer is clearly described in application EP-A-0 837 331 which can be referred to for further information on the technical and structural context in which said control system is set. The general structure of this automatic analyzer comprises a frame on which are mounted a support turntable for analyte samples, a support turntable for determination reactants, and means for taking a defined quantity of samples and a defined quantity of reactants respectively and for depositing same in a reaction cuvette, these means being of the same type as those that are described in application WO-A-96/14582.

The reactants used are of the magnetic bead type and the apparatus according to the invention comprises means for washing or rinsing these magnetic beads, which are of the same type as those already described in the above international applications and which comprise liquid suction and injection needles, with vertical travel, and permanent magnets arranged on each side of the path of the reaction cuvettes to attract the magnetic beads of the reactants by magnetic attraction, and to fix them temporarily on the walls of the reaction cuvettes. The washing means further comprise a needle for depositing a substrate in the reaction cuvettes, the needle being arranged immediately downstream of the washing liquid injection and suction needles.

The means for optical reading of the determination results, which are of the same type as those already described in application WO-A-00/16075, are arranged on the frame near the injection and washing means. They operate by luminescence.

The apparatus according to the invention further comprises means for transporting sets of reaction cuvettes on a rectangular shaped path, at one end of which means are provided for the automatic feeding of sets of reaction cuvettes and for the injection of these cuvettes.

In this apparatus, a set of reaction cuvettes conveyed into the feed position must travel the complete rectangular path twice for a monoreactant determination, and three times for a bireactant determination, before being ejected. The apparatus according to the invention can, in the same way as described in application WO-A-96/14582, operate at a rate of 120 determinations per hour, in a completely automatic manner.

The present invention relates to a temperature control system, which is installed below the support turntable for determination reactants, not shown in the figures. Obviously, it is conceivable for the temperature control system to be present also in the support turntable for analyte samples or for any other liquid present in the automatic biological analyzer.

Figure 1:
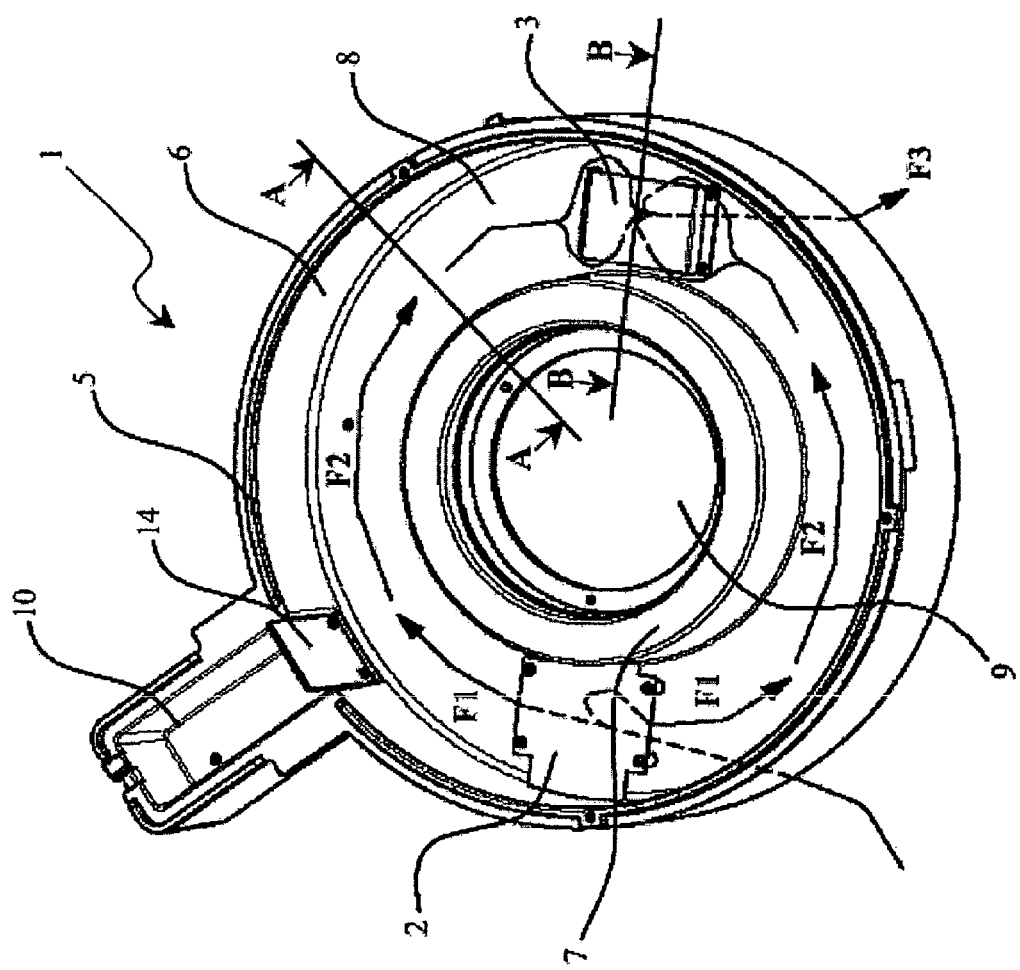
FIG. 1 shows a perspective elevation view of a temperature control system dismantled from the automatic biological analyzer for which it is normally intended.

As shown in FIG. 1, the temperature control system consists of a cover 1 serving to isolate the air streams which will pass along the underside of the turntable supporting the determination reactants.

This cover 1 further comprises a number of walls together forming a ring, at the center of which a central opening 9 is present. Structurally, the central opening 9 permits in particular the passage of a rotary drive shaft, for example for the turntable present on top of the cover 1, or any other drive system for said turntable. This annular shape is obtained by the assembly of an outer vertical wall 6 and an inner vertical wall 7 connected together by a lower horizontal wall 8. It is perfectly conceivable to have a shape that is different to minimize the angles in which the air and hence the temperature cannot easily be adjusted or controlled.

On the periphery of this cover 1, that is, in the outer vertical wall 6, a small cover 10 is present, with the function of receiving a bar code reader (not shown) or any equivalent device, permitting the reading of the data present on the reactant jars. The small cover 10 is separated from the cover 1 by a vertical wall 14 of transparent material, which, while allowing the beam of the bar code reader to pass through, prevents the passage of the air circulating within the cover 1.

On the bottom of the cover 1, that is, on the upper part of the lower horizontal wall 8, which is substantially flat, are two air deflectors 2 and 3 permitting climate-control, and deflectors 2 and 3 which are described below in relation to FIGS. 2 and 3. However, under these deflectors 2 and 3 there are openings 15, not shown in this FIG. 1, which are located along the circular path 4 defined by the walls 6, 7 and 8, said openings 15 being present under each deflector 2 and 3 and permitting, on the one hand, the admission of cold air along F1 and, on the other, the exit of hotter air along F3. Air admission along F1 occurs under the inlet deflector 2 while air exit along F3 occurs under the outlet deflector 3. As for the circular air transfer path 4, the air travels along F2 from the inlet deflector 2 toward the outlet deflector 3, obviously via the openings 15.

Along the circular air transfer path 4, the air stream which is hence at the preservation temperature of the reactants located in the upper turntable, this air transfer has the numeral F2 and follows this circular path 4. Thus, the air transfer F2 occurs along two paths on either side of the central opening 9. It may also be observed that the outer vertical wall 6, in its upper extension, has a circular groove 16 which, when the unit is in place in the automatic analyzer, serves to seal the circular path 4 from the exterior and from the turntable located on top of it, not shown in the figures. This seal serves to prevent the air stream from coming into contact with the tops of the reactant containers, which are in the open air, and prevents the evaporation of said reactants.

Figure 2:
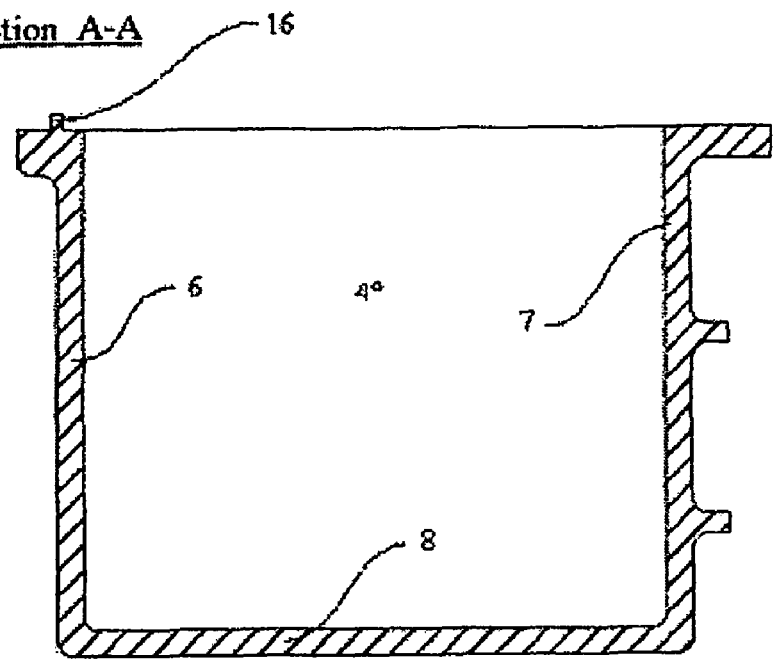
FIG. 2 shows a cross section on A-A of FIG. 1.

With reference to FIG. 2, this is a cross sectional view on A-A of FIG. 1. This figure clearly highlights the assembly of the components of the cover 1, including the outer vertical wall 6, inner vertical wall 7 and lower horizontal wall 8 bounding the circular air transfer path 4. The outer vertical wall 6 is surmounted by the circular groove 16 constituting sealing means 5, when the cover 1 is fixed under the support turntable for the determination reactants.

Figure 3:
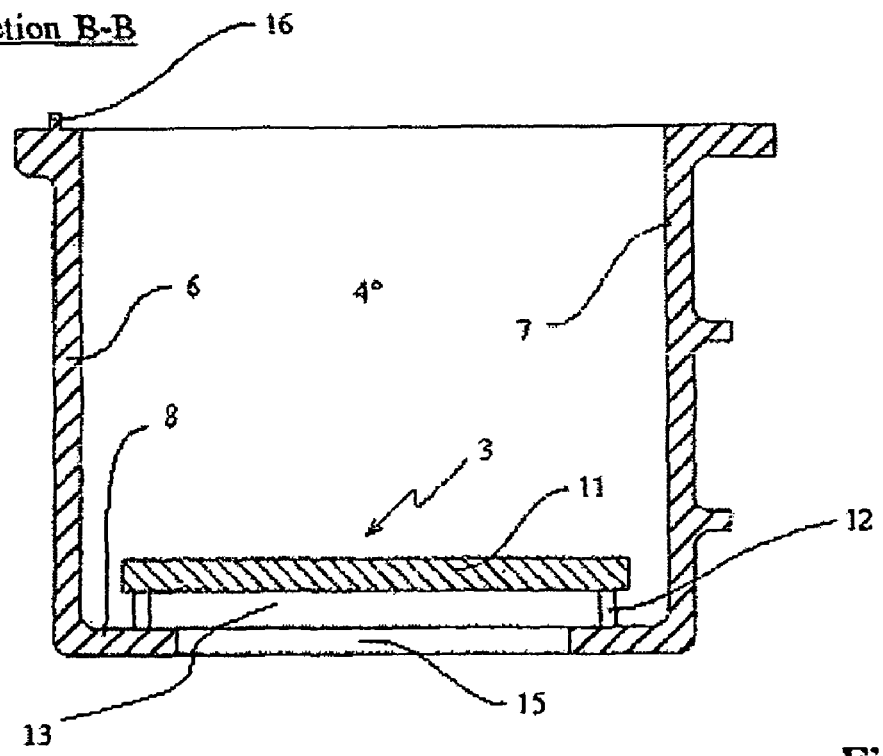
FIG. 3 shows a cross section on B-B of FIG. 1 through the outlet air deflector.

FIG. 3 is substantially identical but shows the cross section B-B of FIG. 1, a cross section made through the air deflectors and more precisely through the outlet air deflector marked 3. Here, the lower horizontal wall 8 comprises an opening 15 located along the circular path 4 under the air deflector 3. This air deflector 3 consists of an upper plate 11 and a number of spacers 12, connecting the wall 8 to the plate 11. The space 13 thus created permits the passage of air along F3 as well as the regulation of the flow rate, whether at the inlet, in respect of the other deflector 2 or in respect of the outlet under the deflector 3. This feature thus makes it possible, when air is blown in under the deflector 2, to obtain a regulation with a thermal variation that is lower than in the absence of said deflectors 2 and 3. Thus, use of the automatic analyzer, in the absence of deflectors, has demonstrated a temperature difference of 5° C. between the air entering along F1 and the air exiting along F3. This difference is only 3° C. when the deflectors 2 and 3 are present. This is equivalent to stating that if the temperature must be a temperature of 14° C., it suffices to have a temperature of 12.5° C. at the inlet of the deflector 2 to obtain an outlet temperature of 15.5° C., which constitutes an acceptable range of values for an automatic biological analyzer according to the present invention. In this case, the biological results are significantly more repetitive and constant.

REFERENCE NUMBERS

1. Cover of refrigeration system
2. Inlet deflector
3. Outlet deflector
4. Circular air transfer path
5. Sealing means
6. Outer vertical wall
7. Inner vertical wall
8. Lower horizontal wall
9. Central opening
10. Cover for bar code reader
11. Upper plate of deflector 2 or 3
12. Spacers connecting wall 8 to plate 11
13. Space created by the spacers 12
14. Transparent vertical wall
15. Opening located on the circular path 4 under the air deflector 3
16. Circular groove for sealing the circular air transfer path 4
F1. Cold air inlet
F2. Air transfer at preservation temperature of biological products
F3. Hot air outlet

The invention claimed is:

1. A system for temperature control within an automatic biological analyzer, the automatic analyzer including at least a support turntable for reactants, the temperature control system being connected to a lower part of the support turntable for the reactants, and comprising:
   at least one inlet air deflector;
   at least one outlet air deflector;
   a circular air transfer path positioned between the inlet air deflector and the outlet air deflector; and
   a cover having a lower horizontal wall that is perforated with at least two openings located substantially at 180° with respect to one another along the circular path, the at least one inlet air deflector and the at least one outlet air deflector being arranged on an upper side of the horizontal wall, each air deflector being positioned over a different one of the at least two openings,
   wherein air circulates in the circular path, thereby permitting a reduction in thermal variation between inlet air and outlet air temperatures within the temperature control system.

2. The system as claimed in claim 1, wherein the cover is formed of substantially annular shape with a U-shaped cross section.

3. The system as claimed in claim 2, wherein the cover further comprises an outer vertical wall and an inner vertical wall.

4. The system as claimed in claim 2, wherein each air deflector includes an upper plate and at least one spacer connecting the horizontal wall to the upper plate.

5. The system as claimed in claim 2, wherein a lower part of the support turntable for the reactants is perforated and extends into the temperature control system.

6. The system as claimed in claim 1, wherein each air deflector includes an upper plate and at least one spacer connecting the horizontal wall to the upper plate.

7. The system as claimed in claim 6, wherein the upper plate is substantially parallel to the upper side of the horizontal wall.

8. The system as claimed in claim 7, wherein a lower part of the support turntable for the reactants is perforated and extends into the temperature control system.

9. The system as claimed in claim 6, wherein a lower part of the support turntable for the reactants is perforated and extends into the temperature control system.

10. The system as claimed in claim 1, wherein a lower part of the support turntable for the reactants is perforated and extends into the temperature control system.

11. The system as claimed in claim 10, wherein the reactants present in containers are only present in openings in the perforated support turntable.

12. The system as claimed in claim 11, wherein the containers are one of bottles or jars.

* * * * *